(12) United States Patent
Banik et al.

(10) Patent No.: US 8,580,524 B2
(45) Date of Patent: Nov. 12, 2013

(54) GALACTOSE-ALPHA-1,3-GALACTOSE-MACROMOLECULE CONJUGATES AND METHODS EMPLOYING SAME

(75) Inventors: Utpal Banik, Sunnyvale, CA (US); Ramon Evangelista, Laguna Hills, CA (US); We-Xing Gan, Simi Valley, CA (US)

(73) Assignee: Siemens Healthcare Diagnostics Inc, Tarrytown, NY (US)

( * ) Notice: Subject to any disclaimer, the term of this patent is extended or adjusted under 35 U.S.C. 154(b) by 0 days.

(21) Appl. No.: 13/466,614

(22) Filed: May 8, 2012

(65) Prior Publication Data
US 2012/0219975 A1 Aug. 30, 2012

Related U.S. Application Data

(62) Division of application No. 12/625,805, filed on Nov. 25, 2009, now Pat. No. 8,198,035.

(51) Int. Cl.
*G01N 33/53* (2006.01)
(52) U.S. Cl.
USPC ............................................. 435/7.1; 425/7.2
(58) Field of Classification Search
None
See application file for complete search history.

(56) References Cited

U.S. PATENT DOCUMENTS

| | | | |
|---|---|---|---|
| 4,528,267 A | 7/1985 | Calenoff et al. | |
| 4,539,292 A | 9/1985 | Reid et al. | |
| 4,844,966 A | 7/1989 | Calenoff et al. | |
| 4,845,027 A | 7/1989 | Calenoff et al. | |
| 4,849,337 A | 7/1989 | Calenoff et al. | |
| 4,968,633 A | 11/1990 | Marcucci | |
| 5,639,601 A | 6/1997 | Saeki et al. | |
| 5,874,228 A | 2/1999 | Delespesse | |
| 6,528,325 B1 | 3/2003 | Hubscher et al. | |
| 7,229,770 B1 | 6/2007 | Price et al. | |
| 2003/0216319 A1* | 11/2003 | Cloos et al. | ...................... 514/13 |
| 2004/0009584 A1 | 1/2004 | Mitra et al. | |
| 2005/0170443 A1 | 8/2005 | Cantor | |
| 2005/0226884 A1 | 10/2005 | Price et al. | |
| 2006/0013810 A1 | 1/2006 | Johnson et al. | |

FOREIGN PATENT DOCUMENTS

WO   WO 2008/101177 A2   8/2008

OTHER PUBLICATIONS

Pang et al. (Clinical Chem 2005 vol. 51, p. 1029-1031).*
Christine H. Chung, et al., Cetuximab-induced Anaphylaxis and IgE Specific for Galactose-alpha-1,3-galactose, N Engl J Med., Mar. 13, 2008, 358(11): 1109-1117, NIH Public Access, Author Manuscript.

* cited by examiner

*Primary Examiner* — Jacob Cheu
(74) *Attorney, Agent, or Firm* — Theodore J. Leitereg

(57) ABSTRACT

Methods and reagents are disclosed for conducting assays for IgE. Embodiments of the present reagents comprise a conjugate of a macromolecule and a compound comprising a galactose-α-1,3-galactose epitope. Embodiments of the present methods are directed to determining the presence and/or amount of an IgE specific for a galactose-α-1,3-galactose epitope in a sample. A combination is provided in a medium, which comprises the sample and a reagent for determining the presence and/or amount of an IgE specific for a galactose-α-1,3-galactose epitope in a sample wherein the reagent comprises a conjugate of a macromolecule and a compound comprising a galactose-α-1,3-galactose epitope. The combination is subjected to conditions for binding of the IgE to the reagent to form a complex. The presence and/or amount of the complex are detected and the amount of the complex is related to the presence and/or amount of IgE in the sample.

8 Claims, No Drawings

GALACTOSE-ALPHA-1,3-GALACTOSE-MACROMOLECULE CONJUGATES AND METHODS EMPLOYING SAME

CROSS-REFERENCE TO RELATED APPLICATION

This application is a Divisional of U.S. patent application Ser. No. 12/625,805 filed on Nov. 25, 2009.

BACKGROUND

This invention relates to reagents for use in methods, compositions and kits for determining specific IgE against the disaccharide epitope galactose-α-1,3-galactose in a sample.

Diagnosis of disease and determination of treatment efficacy are important tools in medicine. In particular, detection of IgE production in an animal can be indicative of disease. Immunoglobulin E (IgE) is the antibody subclass responsible for, among other things, allergic diseases and anaphylactic shock reactions. Measurement of IgE levels in the blood, tissue and body fluids of mammals is generally required for the accurate diagnosis of diseases relating to IgE production. Such diseases include, for example, allergy, atopic disease, hyper IgE syndrome, internal parasite infections and B cell neoplasia. In addition, detection of IgE production in an animal following a treatment involving administration of a medicament is indicative of the efficacy of the treatment, such as when using treatments intended to disrupt IgE production.

Cetuximab, a chimeric mouse-human IgG1 monoclonal antibody against the epidermal growth factor receptor, is approved by the Food and Drug Administration (FDA) for use in colorectal cancer that has spread to other parts of the body. A certain percentage of patients that receive cetuximab experience an adverse reaction to the drug. It is known that the presence of IgE antibodies specific for an oligosaccharide, galactose-α-1,3-galactose, which is present on the Fab portion of the cetuximab heavy chain, can lead to anaphylaxis and other adverse reactions in patients undergoing cetuximab therapy.

SUMMARY

One embodiment of the present invention is a reagent for determining the presence and/or amount of an IgE specific for a galactose-α-1,3-galactose epitope in a sample. The reagent comprises a conjugate of a macromolecule and a compound comprising a galactose-α-1,3-galactose epitope.

Another embodiment of the present invention is a method for determining the presence and/or amount of an IgE specific for a galactose-α-1,3-galactose epitope in a sample. A combination is provided in a medium, which comprises the sample and a reagent for determining the presence and/or amount of an IgE specific for a galactose-α-1,3-galactose epitope wherein the reagent comprises a conjugate of a macromolecule and a compound comprising a galactose-α-1,3-galactose epitope. The combination is subjected to conditions for binding of the IgE to the reagent to form a complex. The presence and/or amount of the complex are detected and the amount of the complex is related to the presence and/or amount of IgE in the sample.

DETAILED DESCRIPTION OF SPECIFIC EMBODIMENTS

General Discussion

Embodiments of the present methods and reagents are concerned with reagents for determining the presence and/or amount of an IgE specific for a galactose-α-1,3-galactose epitope in a sample suspected of containing the IgE specific for a galactose-α-1,3-galactose epitope. The reagent comprises a conjugate of a macromolecule and a compound comprising a galactose-α-1,3-galactose epitope. The reagent can be employed in a method for determining the presence and/or amount of the IgE specific for a galactose-α-1,3-galactose epitope in a patient's sample. In some embodiments the patients are undergoing cetuximab treatment and the presence and/or amount of the IgE in the sample provides an assessment of the patient's hypersensitivity to cetuximab. In the latter instance, steps can be taken to provide alternate treatments for the patient.

The term "compound comprising a galactose-α-1,3-galactose epitope" includes galactose-α-1,3-galactose and derivatives of galactose-α-1,3-galactose, oligomers (e.g., dimers, trimers) of galactose-α-1,3-galactose and glycopeptides bearing oligosaccharides with terminal galactose-α-1,3-galactose. Derivatives of galactose-α-1,3-galactose include, for example, amides, esters, ethers, amines, sulfonamides, thioethers, acetals, carbamates, ureas and amidines. Examples of compounds comprising a galactose-α-1,3-galactose epitope, by way of illustration and not limitation, include galactose-α-1,3-galactose (α1-3 galactobiose) (Galα1-3Gal) and derivatives thereof such as, for example, glucosamine derivatives, linear B-2 trisaccharide (Galα1-3Galβ1-4GlcNAc), linear B-6 trisaccharide (Galα1-3Galβ1-4Glc) and derivatives thereof, α1-3 galactobiosyl β-methyl glycoside, α1-3, β1-4 galactotriose (Galα1-3Galβ1-4Gal), galactotetraose (Galα1-3Galβ1-4Galα1-3-D-Gal), and derivatives of the above such as, e.g., amino acid derivatives (e.g., dodecalysine, glycine) and glycopeptides with galactose-α-1,3-galactose.

The macromolecule employed in embodiments of a conjugate of a macromolecule and a compound comprising a galactose-α-1,3-galactose epitope is a molecule that has a molecular weight of at least about 10,000, or at least about 50,000, or at least about 100,000, or at least about 500,000, or at least about 1,000,000, for example. The molecular weight may be in a range of about 10,000 to about 10,000,000 or more, or about 10,000 to about 8,000,000, or about 10,000 to about 6,000,000, or about 10,000 to about 5,000,000 or about 10,000 to about 4,000,000, or about 10,000 to about 3,000,000 or about 10,000 to about 2,000,000, or about 10,000 to about 1,000,000, or about 50,000 to about 10,000,000 or more, or about 50,000 to about 8,000,000, or about 50,000 to about 6,000,000, or about 50,000 to about 5,000,000 or about 50,000 to about 4,000,000, or about 50,000 to about 3,000,000 or about 50,000 to about 2,000,000, or about 50,000 to about 1,000,000, or about 100,000 to about 10,000,000 or more, or about 100,000 to about 8,000,000, or about 100,000 to about 6,000,000, or about 100,000 to about 5,000,000 or about 100,000 to about 4,000,000, or about 100,000 to about 3,000,000 or about 100,000 to about 2,000,000, or about 100,000 to about 1,000,000, and the like.

In some embodiments the macromolecule may be polymeric. The polymeric macromolecule is generally about 10 to about 10,000 monomer units in length, or about 100 to about 10,000 monomer units in length, or about 500 to about 10,000 monomer units in length, or about 1,000 to about 10,000 monomer units in length, or about 2,000 to about 10,000 monomer units in length, or about 3,000 to about 10,000 monomer units in length, or about 5,000 to about 10,000 monomer units in length, or about 10 to about 8,000 monomer units in length, or about 100 to about 8,000 monomer units in length, or about 1,000 to about 8,000 monomer units in length, or about 100 to about 7,000 monomer units in length, for example. The number of monomer units depends on the number of atoms in the monomer unit chain, the composition of the monomer unit, and so forth. The monomer units may be the same (repeating units of the same monomer) or may be different from one another (such as, for example, in a peptide or protein).

In some embodiments one or more of the monomer units of the polymeric macromolecule comprise carbon atoms and one or more heteroatoms such as, for example, oxygen, sulfur, nitrogen, phosphorus, and the like. The monomer units may comprise about 2 to about 50 atoms or more, or 5 to about 50 atoms, or about 10 to about 50 atoms, or about 20 to about 50 atoms, or about 30 to about 50 atoms, or about 2 to about 40 atoms or more, or 5 to about 40 atoms, or about 10 to about 40 atoms, or about 20 to about 40 atoms, or about 30 to about 40 atoms, or about 2 to about 30 atoms or more, or 5 to about 30 atoms, or about 10 to about 30 atoms, or about 20 to about 30 atoms, not counting hydrogen and may comprise a chain of from 2 to about 30 atoms, or about 5 to about 30 atoms or more, or 10 to about 30 atoms, or about 15 to about 30 atoms, or about 20 to about 30 atoms, or about 2 to about 25 atoms or more, or 5 to about 25 atoms, or about 10 to about 25 atoms, or about 15 to about 25 atoms, or about 20 to about 25 atoms, or about 2 to about 20 atoms or more, or 5 to about 20 atoms, or about 10 to about 20 atoms, or about 15 to about 20 atoms, or about 2 to about 15 atoms, or about 5 to about 15 atoms, or about 10 to about 15 atoms, each independently selected from the group normally consisting of carbon, oxygen, sulfur, nitrogen, and phosphorous.

The number of heteroatoms in a monomer unit of the polymeric macromolecule depends on the total number of atoms in the monomer unit and may range from about 0 to about 20, or about 0 to about 15, or about 0 to about 10, or about 0 to about 5, or about 1 to about 20, or about 1 to about 15, or about 1 to about 10, or about 1 to about 5, or about 2 to about 20, or about 2 to about 15, or about 2 to about 10, or about 2 to about 5, or about 5 to about 20, or about 5 to about 15, or about 5 to about 10, and the like. When heteroatoms are present, oxygen is normally present as oxo or oxy, bonded to carbon, sulfur, nitrogen or phosphorous, nitrogen is normally present as azo, cyano, isocyano, nitro, nitroso, amido or amino, normally bonded to carbon, oxygen, sulfur or phosphorous; sulfur is analogous to oxygen; while phosphorous is bonded to carbon, sulfur, oxygen or nitrogen, usually as phosphonate and phosphate mono- or diester.

The polymeric macromolecule may be a naturally-occurring material or a synthetic construct. In some embodiments the polymeric macromolecule is a polypeptide. Examples of naturally-occurring polypeptides, by way of illustration and not limitation, include proteins such as, e.g., albumins and globulins, which may be from a human or other animal source. The albumins include, for example, human serum albumin and bovine serum albumin. The globulins include, for example, gamma globulins and immunoglobulins.

Examples of other polymeric macromolecules, by way of illustration and not limitation, include dendrimers, polymeric carboxylates (e.g., polyaspartic acid, polyglutamic acid, polygalacturonic acid, polymethacrylic acid, etc.), polymeric amines (e.g., polyethylene amine, polylysine, polyglutamine, polyethylene imine, polyallylamine, etc.), polymeric ethers (polyethyleneglycols or polyethylene oxide, etc.), polymeric thioethers (e.g., polyethylene thioethers, etc.), polymeric sulfhydryls (e.g. polycysteine) and so forth.

In some embodiments of the present conjugates, the macromolecule is covalently bound to the compound comprising a galactose-α-1,3-galactose epitope. Covalent binding may be achieved by a bond or a linking group. In some embodiments, the linking group has a molecular weight less than about 2000, or less than about 1500, or less than about 1000, or less than about 500, for example. Such linking groups may comprise about 2 to about 200 atoms, or 4 to about 150 atoms, or about 5 to about 100 atoms, not counting hydrogen and may comprise a chain of from 2 to about 100 atoms, or 3 to about 90 atoms, or about 4 to about 80 atoms, or about 5 to about 70 atoms, for example, each independently selected from the group normally consisting of carbon, oxygen, sulfur, nitrogen, and phosphorous. The number of heteroatoms in such linking groups is dependent on the size of the linking group and will normally range from about 0 to about 30, 1 to about 25, or about 2 to about 20, or about 2 to about 150, or about 2 to about 10, or about 3 to about 10, for example.

Common functionalities in forming a covalent bond between the linking group and the molecules to be conjugated are alkylamine, amidine, thioamide, sulfonamide, ether, ester, urea, thiourea, guanidine, azo, thioether and carboxylate, sulfonate, and phosphate esters, amides and thioesters. For the most part, when a linking group has a linking functionality (functionality for reaction with a moiety) such as, for example, a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities are linked to amine groups, carboxyl groups, active olefins, alkylating agents, e.g., bromoacetyl. Where an amine and carboxylic acid, or its nitrogen derivative or phosphoric acid derivative, are linked, amides, amidines and phosphoramides are formed respectively. Where mercaptan and activated olefin are linked, thioethers are formed. Where a mercaptan and an alkylating agent are linked, thioethers are formed. Where aldehyde and an amine are linked under reducing conditions, an alkylamine is formed. Where a ketone or aldehyde and a hydroxylamine (including derivatives thereof where a substituent is in place of the hydrogen of the hydroxyl group) are linked, an oxime functionality (=N—O—) is formed. Where a carboxylic acid or phosphate acid and an alcohol are linked, esters are formed.

In some embodiments the macromolecule is non-covalently bound to the compound comprising a galactose-α-1,3-galactose epitope. Non-covalent binding may be realized in some embodiments by employing members of a specific binding pair ("sbp members"). A specific binding pair for use in the present embodiments for non-covalent binding is selected from the group consisting of (i) small molecule and binding partner for the small molecule and (ii) large molecule and binding partner for the large molecule. In some embodiments, the small molecule has a molecular weight less than about 2000, or less than about 1500, or less than about 1000, or less than about 500, or less than about 400, or less than about 300, for example. Examples of small molecule-binding partner for the small molecule pairs, by way of illustration and not limitation, include biotin-binding partner for biotin (e.g., avidin, streptavidin, antibody for biotin, etc.), digoxin-binding partner for digoxin (e.g., antibody for digoxin, etc.), fluorescein-binding partner for fluorescein (antibody for fluorescein, etc.), rhodamine-binding partner for rhodamine (e.g., antibody for rhodamine), peptide-binding partner for the peptide (antibody for the peptide, etc.), analyte-specific binding partners (e.g., intrinsic factor for B12, folate binding factor for folate) and so forth.

In some embodiments of a specific binding pair for use in the present embodiments for conjugating the macromolecule and the compound comprising a galactose-α-1,3-galactose epitope, the molecular weight of the large molecule is greater than about 2,000, or greater than about 5,000, or greater than about 10,000, or greater than about 50,000, or greater than about 100,000, or greater than about 500,000, or greater than about 1,000,000, or greater than about 5,000,000 or greater than about 10,000,000, or the like. Examples of large molecule-binding partner for the large molecule pairs, by way of illustration and not limitation, include members of an immunological pair such as antigen-antibody, hormone-hormone receptors, nucleic acid duplexes, IgG-protein A, polynucleotide pairs such as DNA-DNA, DNA-RNA, other receptors and ligands, and the like.

In some embodiments the macromolecule is a particle, which may be comprised of an organic or inorganic, solid or fluid, water insoluble material, which may be transparent or partially transparent. The particles generally have an average diameter of at least about 0.02 microns and not more than about 100 microns. In some embodiments, the particles have an average diameter from about 0.05 microns to about 20 microns or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, streptococcus, *Staphylococcus aureus, E. coli*, viruses, and the like. The particles can also be particles comprised of organic and inorganic polymers, liposomes, latex particles, magnetic or non-magnetic particles, phospholipid vesicles, chylomicrons, lipoproteins, and the like. In some embodiments, the particles are chrome particles or latex particles.

As mentioned above, embodiments of the conjugates of a macromolecule and a compound comprising a galactose-α-1,3-galactose epitope may employed in methods for determining the presence and/or amount of an IgE specific for a galactose-α-1,3-galactose epitope in a sample. A combination is provided in a medium, which comprises the sample and a reagent for determining the presence and/or amount of an IgE specific for a galactose-α-1,3-galactose epitope in a sample wherein the reagent comprises a conjugate of a macromolecule and a compound comprising a galactose-α-1,3-galactose epitope. The combination is subjected to conditions for binding of the IgE to the conjugate reagent to form a complex. The presence and/or amount of the complex are detected and the amount of the complex is related to the presence and/or amount of IgE in the sample.

The sample to be analyzed is one that is suspected of containing IgE because the patient may be experiencing a factor that would be responsible for IgE production such as, for example, an IgE related disease, e.g., an allergic disease, or the consumption of a medication. The samples are preferably from a mammalian subject, e.g., humans or other animal species and include biological fluids such as whole blood, serum, plasma, sputum, lymphatic fluid, semen, vaginal mucus, feces, urine, spinal fluid, saliva, stool, cerebral spinal fluid, tears, mucus, and the like; biological tissue such as hair, skin, sections or excised tissues from organs or other body parts; and so forth. In many instances, the sample is whole blood, plasma or serum.

The sample can be prepared in any convenient medium. Conveniently, the sample may be prepared in an assay medium, which is discussed more fully hereinbelow. In some instances a pretreatment may be applied to the sample such as, for example, to lyse blood cells. Such pretreatment is usually performed in a medium that does not interfere subsequently with an assay. An aqueous medium is preferred for the pretreatment.

The assays are normally carried out in an aqueous buffered medium at a moderate pH, generally that which provides optimum assay sensitivity. The aqueous medium may be solely water or may include from 0.1 to about 40 volume percent of a cosolvent. The pH for the medium will usually be in the range of about 4 to about 11, more usually in the range of about 5 to about 10, and preferably in the range of about 6.5 to about 9.5. The pH will usually be a compromise between optimum binding of the binding members of any specific binding pairs, the pH optimum for other reagents of the assay such as members of the signal producing system, and so forth. Various buffers may be used to achieve the desired pH and maintain the pH during the determination. Illustrative buffers include borate, phosphate, carbonate, tris, barbital, PIPES, HEPES, MES, ACES, MOPS, BICINE, and the like. The particular buffer employed is not critical, but in an individual assay one or another buffer may be preferred.

Various ancillary materials may be employed in the assay methods. For example, in addition to buffers the medium may comprise stabilizers for the medium and for the reagents employed. In some embodiments, in addition to these additives, proteins may be included, such as albumins; organic solvents such as formamide; quaternary ammonium salts; polyanions such as dextran sulfate; binding enhancers, e.g., polyalkylene glycols; polysaccharides such as dextran, trehalose, or the like. The medium may also comprise agents for preventing the formation of blood clots. Such agents are well known in the art and include, for example, EDTA, EGTA, citrate, heparin, and the like. The medium may also comprise one or more preservatives as are known in the art such as, for example, sodium azide, neomycin sulfate, PROCLIN® 300, Streptomycin, and the like. Any of the above materials, if employed, is present in a concentration or amount sufficient to achieve the desired effect or function.

The sample and a reagent for determining the presence and/or amount of an IgE specific for a galactose-α-1,3-galactose epitope in a sample is combined in the assay medium. The reagent comprises a conjugate of a macromolecule and a compound comprising a galactose-α-1,3-galactose epitope. IgE in the sample, if present, binds to the reagent. Depending on the nature of the assay employed, the reagent that comprises the conjugate may also comprise one or more components such as, for example, a small molecule, a particle, a member of a signal producing system, and the like. Furthermore, again depending on the nature of the assay employed, other reagents may also be included in the initial combination or added subsequently. Such reagents include additional binding agents such as, for example, one or more antibodies, e.g., antibodies for IgE, members of a signal producing system and so forth.

One or more incubation periods may be applied to the medium at one or more intervals including any intervals between additions of various reagents employed in an assay including those mentioned above. The medium is usually incubated at a temperature and for a time sufficient for binding of various components of the reagents and binding of IgE in the sample to occur. Moderate temperatures are normally employed for carrying out the method and usually constant temperature, preferably, room temperature, during the period of the measurement. Incubation temperatures normally range from about 5° to about 99° C., usually from about 15° C. to about 70° C., more usually 20° C. to about 45° C. The time period for the incubation is about 0.2 seconds to about 24 hours, or about 1 second to about 6 hours, or about 2 seconds to about 1 hour, or about 1 to about 15 minutes. The time period depends on the temperature of the medium and the rate of binding of the various reagents, which is determined by the association rate constant, the concentration, the binding constant and dissociation rate constant.

General Description of Assays for an IgE Analyte Utilizing the Present Reagents

The conjugate of the macromolecule and a compound comprising a galactose-α-1,3-galactose epitope may be employed in the determination of IgE using a number of different assay formats. In general, in such assays the reagents comprise, among others, the above conjugate. A sample suspected of containing IgE is combined in an assay medium with the above conjugate, which may be added as a preformed reagent or which may be formed in situ by, for example, the binding of specific binding pair members. For example, one member of the specific binding pair may be attached to the macromolecule and the other member to a compound comprising a galactose-α-1,3-galactose epitope. A determination is made of the extent of binding between the IgE and the present conjugate reagent. A labeled reagent specific for IgE may also be employed in some embodiments for detection of the binding event between IgE and the conjugate reagent. The assay can be performed either without separation (homogeneous) or with separation (heterogeneous) of any of the assay components or products. Heterogeneous assays usually involve one or more separation steps and can be competitive or non-competitive.

Immunoassays may involve labeled or non-labeled reagents. Immunoassays involving non-labeled reagents usually comprise the formation of relatively large complexes involving one or more antibodies. Such assays include, for example, immunoprecipitin and agglutination methods and corresponding light scattering techniques such as, e.g., nephelometry and turbidimetry, for the detection of antibody complexes. Labeled immunoassays include chemiluminescence immunoassays, enzyme immunoassays, fluorescence polarization immunoassays, radioimmunoassay, inhibition assay, induced luminescence, fluorescent oxygen channeling assay, and so forth.

One general group of immunoassays in which the conjugate of a macromolecule and a compound comprising a galactose-α-1,3-galactose epitope may be employed to determine the presence and/or amount of IgE in a sample includes immunoassays using a limited concentration of the present conjugate reagent. Another group of immunoassays involves the use of an excess of one or more of the principal reagents such as, for example, an excess of the present conjugate reagent. Another group of immunoassays are separation-free homogeneous assays in which the labeled reagents modulate the label signal upon binding of the present conjugate and IgE in the sample.

As mentioned above, the assays can be performed either without separation (homogeneous) or with separation (heterogeneous) of any of the assay components or products. Homogeneous immunoassays are exemplified by the EMIT® assay (Siemens Healthcare Diagnostics Inc., Deerfield, Ill.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; enzyme immunoassays such as the enzyme linked immunosorbant assay ("ELISA"). Exemplary of heterogeneous assays are the radioimmunoassay, disclosed in Yalow, et al., J. Clin. Invest. 39:1157 (1960). The above disclosures are all incorporated herein by reference.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"), etc.; and the like.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); and so forth. Other types of assays include immunosensor assays involving the monitoring of the changes in the optical, acoustic and electrical properties of the present conjugate upon the binding of IgE. Such assays include, for example, optical immunosensor assays, acoustic immunosensor assays, semiconductor immunosensor assays, electrochemical transducer immunosensor assays, potentiometric immunosensor assays, amperometric electrode assays.

Heterogeneous assays usually involve one or more separation steps and can be competitive or non-competitive. A variety of competitive and non-competitive heterogeneous assay formats are disclosed in Davalian, et al., U.S. Pat. No. 5,089,390, column 14, line 25 to column 15, line 9, incorporated herein by reference. In a typical competitive heterogeneous assay, a support having the present conjugate bound thereto is contacted with a medium containing the sample suspected of containing IgE and IgE conjugated to a detectable label such as an enzyme. IgE in the sample competes with the IgE conjugate bearing the detectable label for binding to the present conjugate. After separating the support and the medium, the label activity of the support or the medium is determined by conventional techniques and is related to the amount of IgE in the sample.

In a typical non-competitive sandwich assay, an immune sandwich complex is formed in an assay medium. The complex comprises the IgE analyte, a conjugate of a macromolecule and a compound comprising a galactose-α-1,3-galactose epitope and an antibody that binds to the IgE analyte or a complex of the IgE analyte and the present conjugate reagent. Subsequently, the immune sandwich complex is detected and is related to the amount of IgE analyte in the sample. The immune sandwich complex is detected by virtue of the presence in the complex of a label wherein either or both the present conjugate reagent and the antibody for IgE contain labels or substituents capable of combining with labels. In one approach in a sandwich assay, a first incubation of unlabeled conjugate reagent coupled to a solid support such as a particle is contacted with a medium containing a sample suspected of containing the IgE analyte. After a wash and separation step, the support is contacted with a medium containing an antibody for IgE, which contains a label such as an enzyme, for a second incubation period. The support is again washed and separated from the medium and either the medium or the support is examined for the presence of label. The presence and amount of label is related to the presence or amount of the IgE analyte.

In a variation of the above sandwich assay, the sample suspected of containing IgE in a suitable medium is contacted with labeled antibody for the IgE and incubated for a period of time. Then, the medium is contacted with a support to which is bound a conjugate of a macromolecule and a compound comprising a galactose-α-1,3-galactose epitope. After an incubation period, the support is separated from the medium and washed to remove unbound reagents. The support or the medium is examined for the presence of the label, which is related to the presence or amount of IgE. In another variation of the above, the sample, the present conjugate bound to a support and the labeled antibody are combined in a medium and incubated in a single incubation step. Separation, wash steps and examination for label are as described above.

In many of the assays discussed herein, a label is employed; the label is usually part of a signal producing system ("sps"). The nature of the label is dependent on the particular assay format. An sps usually includes one or more components, at least one component being a detectable label, which generates a detectable signal that relates to the amount of bound and/or unbound label, i.e. the amount of label bound or not bound to the IgE analyte being detected or to an agent that reflects the amount of the IgE analyte to be detected. The label is any molecule that produces or can be induced to produce a signal, and may be, for example, an enzyme, a fluorescer, a chemiluminescer, a photosensitizer, or a radiolabel. Thus, the signal is detected and/or measured by detecting enzyme activity, luminescence, light absorbance or radioactivity, respectively.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; complexes such as those prepared from CdSe and ZnS present in semiconductor nanocrystals known as Quantum dots; chemiluminescers such as isoluminol; sensitizers; coenzymes; enzyme substrates; radiolabels such as $^{125}I$, $^{131}I$, $^{14}C$, $^{3}H$, H, $^{57}Co$ and $^{75}Se$; particles such as latex particles, carbon particles, metal particles including magnetic particles, e.g., chromium dioxide ($CrO_2$) particles, and the like; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19-28, and Boguslaski, et al., U.S. Pat. No. 4,318,980, columns 10-14; suitable fluorescers and chemiluminescers are disclosed in Litman, et al., U.S. Pat. No. 4,275,149, at columns 30 and 31; which are incorporated herein by reference.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include substrates, coenzymes, enhancers, additional enzymes, substances that react with enzymatic products, catalysts, activators, cofactors, inhibitors, scavengers, metal ions, and a specific binding substance required for binding of signal generating substances. A detailed discussion of suitable signal producing systems can be found in Ullman, et al., U.S. Pat. No. 5,185,243, columns 11-13, incorporated herein by reference.

In some embodiments the enzymes are redox enzymes, particularly dehydrogenases such as glucose-6-phosphate dehydrogenase, lactate dehydrogenase, etc., and enzymes that involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horseradish peroxidase, lactoperoxidase, or microperoxidase. Additional enzyme combinations are known in the art. When a single enzyme is used as a label, other enzymes may find use such as hydrolases, transferases, and oxidoreductases, preferably hydrolases such as alkaline phosphatase and beta-galactosidase. Alternatively, luciferases may be used such as firefly luciferase and bacterial luciferase.

Illustrative co-factors and co-enzymes that find use include NAD[H], NADP[H], pyridoxal phosphate, FAD[H], FMN [H], etc., usually coenzymes involving cycling reactions. See, for example, U.S. Pat. No. 4,318,980, the disclosure of which is incorporated herein by reference.

Some known assays utilize a signal producing system (sps) that employs first and second sps members. The designation "first" and "second" is completely arbitrary and is not meant to suggest any order or ranking among the sps members or any order of addition of the sps members in the present methods. The sps members may be related in that activation of one member of the sps produces a product such as, e.g., light, which results in activation of another member of the sps.

In some embodiments of known assays, the sps members comprise a sensitizer such as, for example, a photosensitizer, and the like, and a chemiluminescent composition where activation of the sensitizer results in a product that activates the chemiluminescent composition. The second sps member usually generates a detectable signal that relates to the amount of bound and/or unbound sps member, i.e. the amount of sps member bound or not bound to the IgE analyte being detected or to an agent that reflects the amount of the IgE analyte to be detected. In accordance with embodiments of the present invention, one of either the sensitizer reagent or the chemiluminescent reagent comprises the present conjugate reagent. Examples of photosensitizers and chemiluminescent reagents that may be utilized are those set forth in U.S. Pat. Nos. 5,340,716 and 6,251,581, the relevant disclosures of which are incorporated herein by reference.

In a particular embodiment, an induced luminescence immunoassay may be employed where the assay utilizes a conjugate of a macromolecule and galactose-α-1,3-galactose. The induced luminescence immunoassay is referred to in U.S. Pat. No. 5,340,716 (Ullman), which disclosure is incorporated herein by reference. In one approach in accordance with the present embodiments, the assay uses a particle having associated therewith a photosensitizer where the particle is the macromolecule of the present conjugates. The chemiluminescent reagent comprises a binding partner for IgE, for example, antibody for IgE. The galactose-α-1,3-galactose epitope binds to the IgE analyte to form a complex, or binds to a second sbp member to form a complex, in relation to the presence of the IgE analyte. If the IgE analyte is present, the photosensitizer and the chemiluminescent compound come into close proximity by virtue of the binding, to the IgE analyte, of the binding partner for the IgE analyte that is part of the chemiluminescent reagent in accordance with the present embodiments. The photosensitizer generates singlet oxygen and activates the chemiluminescent reagent when the two labels are in close proximity. The activated chemiluminescent reagent subsequently produces light. The amount of light produced is related to the amount of the complex formed, which in turn is related to the amount of IgE analyte present.

In some embodiments of the induced luminescence assay, a photosensitizer particle is employed that is conjugated to avidin or streptavidin. Biotinylated compound comprising a galactose-α-1,3-galactose epitope is also employed. A chemiluminescent reagent that comprises a binding partner for IgE is employed as part of the detection system. The reaction medium is incubated to allow the photo sensitizer particles to bind to the biotinylated compound comprising a galactose-α-1,3-galactose epitope by virtue of the binding between avidin and biotin and to also allow the binding partner for the IgE analyte that is part of the chemiluminescent reagent to bind to the IgE analyte. Then, the medium is irradiated with light to excite the photosensitizer, which is capable in its excited state of activating oxygen to a singlet state. Because the chemiluminescent reagent is now in close proximity to the photosensitizer by virtue of the presence of the analyte, it is activated by the singlet oxygen and emits luminescence. The medium is then examined for the presence and/or the amount of luminescence or light emitted, the presence thereof being related to the presence and/or amount of the IgE analyte.

The concentration of the IgE analyte that may be assayed generally varies from about $10^{-5}$ to about $10^{-17}$ M, more usually from about $10^{-6}$ to about $10^{-14}$ M. Considerations, such as whether the assay is qualitative, semi-quantitative or quantitative (relative to the amount of the IgE analyte present in the sample), the particular detection technique and the expected concentration of the IgE analyte normally determine the concentrations of the various reagents.

The concentrations of the various reagents in the assay medium will generally be determined by the concentration range of interest of the IgE analyte, the nature of the assay, and the like. However, the final concentration of each of the reagents is normally determined empirically to optimize the sensitivity of the assay over the range. That is, a variation in concentration of IgE analyte that is of significance should provide an accurately measurable signal difference. Considerations such as the nature of the signal producing system and the nature of the analytes normally determine the concentrations of the various reagents.

As mentioned above, the sample and reagents are provided in combination in the medium. While the order of addition to the medium may be varied, there will be certain preferences for some embodiments of the assay formats described herein. The simplest order of addition, of course, is to add all the materials simultaneously and determine the effect that the assay medium has on the signal as in a homogeneous assay. Alternatively, each of the reagents, or groups of reagents, can be combined sequentially. In some embodiments, an incubation step may be involved subsequent to each addition as discussed above. In heterogeneous assays, washing steps may also be employed after one or more incubation steps.

Examination Step

In a next step of an assay method, the medium is examined for the presence of a complex comprising the IgE analyte and the conjugate of a macromolecule and a compound comprising a galactose-α-1,3-galactose epitope. The presence and/or amount of the complex indicates the presence and/or amount of the IgE analyte in the sample.

The phrase "measuring the amount of an IgE analyte" refers to the quantitative, semiquantitative and qualitative determination of the analyte. Methods that are quantitative, semiquantitative and qualitative, as well as all other methods for determining the IgE analyte, are considered to be methods of measuring the amount of the IgE analyte. For example, a method, which merely detects the presence or absence of the IgE analyte in a sample suspected of containing the IgE analyte, is considered to be included within the scope of the present invention. The terms "detecting" and "determining," as well as other common synonyms for measuring, are contemplated within the scope of the present invention.

In many embodiments the examination of the medium involves detection of a signal from the medium. The presence and/or amount of the signal is related to the presence and/or amount of the IgE analyte in the sample. The particular mode of detection depends on the nature of the sps. As discussed above, there are numerous methods by which a label of an sps can produce a signal detectable by external means. Activation of a signal producing system depends on the nature of the signal producing system members.

Temperatures during measurements generally range from about 10° to about 70° C. or from about 20° to about 45° C., or about 20° to about 25° C. In one approach standard curves are formed using known concentrations of the IgE analyte. Calibrators and other controls may also be used.

Luminescence or light produced from any label can be measured visually, photographically, actinometrically, spectrophotometrically or by any other convenient means to determine the amount thereof, which is related to the amount of IgE analyte in the medium. The examination for presence and/or amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, and the like.

Kits Comprising Reagents for Conducting Assays

The present conjugate of a macromolecule and a compound comprising a galactose-α-1,3-galactose epitope and other reagents for conducting a particular assay for an IgE analyte may be present in a kit useful for conveniently performing an assay for the determination of an IgE analyte. In some embodiments a kit comprises in packaged combination a biotin-binding partner such as, for example, avidin or streptavidin, associated with a particle, biotinylated conjugate of a macromolecule and a compound comprising a galactose-α-1,3-galactose epitope in accordance with the present embodiments and an enzyme labeled antibody for the IgE analyte. The kit may further include other reagents for performing the assay, the nature of which depend upon the particular assay format.

The reagents may each be in separate containers or various reagents can be combined in one or more containers depending on the cross-reactivity and stability of the reagents. The kit can further include other separately packaged reagents for conducting an assay such as additional sbp members, sps members, ancillary reagents, for example.

The relative amounts of the various reagents in the kits can be varied widely to provide for concentrations of the reagents that substantially optimize the reactions that need to occur during the present methods and further to optimize substantially the sensitivity of an assay. Under appropriate circumstances one or more of the reagents in the kit can be provided as a dry powder, usually lyophilized, including excipients, which on dissolution will provide for a reagent solution having the appropriate concentrations for performing a method or assay in accordance with embodiments of the present invention. The kit can further include a written description of a method in accordance with embodiments of the present invention as described above.

The phrase "at least" as used herein means that the number of specified items may be equal to or greater than the number recited. The phrase "about" as used herein means that the number recited may differ by plus or minus 10%; for example, "about 5" means a range of 4.5 to 5.5. The designations "first" and "second" are used solely for the purpose of differentiating between two items such as, for example, "first sps member" and "second sps member," and are not meant to imply any sequence or order or importance to one item over another. As used herein, the phrase "associated with" includes covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, coating one moiety on another moiety, and so forth.

The following examples further describe specific embodiments of the invention by way of illustration and not limitation and are intended to describe and not to limit the scope of the invention. Parts and percentages disclosed herein are by volume unless otherwise indicated.

EXAMPLES

Materials:

Unless indicated otherwise, reagents were purchased from Sigma-Aldrich (Milwaukee, Wis.) and used as received.

Definitions: HSA=human serum albumin; LC=aminocaproic acid (long chain linker); PBS=phosphate buffered saline, 0.1 M phosphate pH 7.4, 0.15 M NaCl; MALDI-TOF=Matrix Assisted Laser Desorption/Ionization Time-of-Flight; borate buffer=0.1 M borate pH 8.0; phosphate buffer=0.1 M phosphate pH 7.5; GlcNAc=N-acetylglucosamine; NHS=N-hydroxysuccinimide; PMT=photomultiplier tube; kU=kilo unit; mIU=milli-international unit.

Preparation of Biotin-LC-HSA-Galactotetraose Conjugate:

This conjugate was prepared by reductive amination of biotinylated HSA (approximately 6 biotin molecules per HSA) with galactotetraose in the presence of sodium cyanoborohydride. Reductive amination in PBS, pH 7.4 produced an average loading of 5.5 galactotetraose per HSA. Reductive amination in borate buffer, pH 8.0, produced an average of 4.0 galactotetraose attached to each albumin molecule based on MALDI-TOF mass spectral analysis.

Preparation of Biotin-LC-HSA-Linear B2-trisaccharide Conjugate:

This conjugate was prepared by reductive amination between HSA-LC-Biotin and Linear B2 trisaccharide in the presence of sodium cyanoborohydride. The MALDI-TOF mass spectra showed that an average of 1.8 Linear B2 trisaccharide was attached to each HSA molecule.

The reductive amination between synthetic N-terminal biotinylated Dodecalysine and Galactotetraose was conducted in the presence of sodium cyanoborohydride at 37° C. for six days. After lyophilization overnight, the residue was desalted by a 1×12 cm Sephadex G-10 column twice. Two-mL fractions were collected right after void volume as determined with blue dextran. The MALDI-TOF mass spectra show that the reductive amination product is a mixture of conjugates with 2-6 Galactotetraose units attached to dodecalysine. The conjugate with four oligosaccharides attached to the peptide was the most abundant species.

Preparation of Gal$\alpha$1-3Gal$\beta$1-4GlcNAc-HSA-LC-Biotin Conjugate:

This conjugate was prepared by treatment of Gal$\alpha$1,3-Gal$\beta$1-4-GlcNAc-HSA (3-atom spacer) (V-Labs NGP2334, Covington La.) with a 10-fold excess of Biotin-LC-NHS (from Siemens Healthcare Diagnostics, Inc.) in phosphate buffer pH 7.5. The conjugate was isolated by gel filtration through a Sephadex G-25 column using PBS, pH 7.5, with sodium azide as eluting buffer. The MALDI-TOF spectra showed that the average biotin loading was 5.5.

Assay for IgE Analyte:

The experiments were conducted on a Reagent Carousel of the IMMULITE® 2000/2500 3gAllergy assay (Siemens Healthcare Diagnostics Inc., Newark Del.). This assay system measures an immune response, in this case, the amount of immunoglobulin E (IgE), to specific allergen, in patient serum. Both the anti-IgE and the allergen are liquid and are stored in bar-coded vials that fit into the Allergen Wedge on the Reagent Carousel. Any number of biotinylated allergens can be used with the 3gAllergy system. The 3gAllergy assay on the IMMULITE 2000/2500 is a 2-cycle assay. At the start of the first cycle patient serum containing specific IgE and biotinylated allergen wherein the allergen was a compound comprising a galactose-$\alpha$-1,3-galactose epitope (for example, Gal$\alpha$1-3Gal$\beta$1-4GlcNAc-HSA-LC-Biotin Conjugate, Biotin-LC-HSA-Galacto-tetraose Conjugate, or Biotin-LC-HSA-Linear B2-trisaccharide Conjugate) from bar-coded test tubes were added simultaneously to a streptavidin-coated bead. The mixture was incubated for 30 minutes at 37° C. The patient's IgE antibody (Ab) recognizes and binds to the allergen. The IgE Ab/biotinylated allergen complex binds to the streptavidin-coated bead. Unbound material was removed through a wash cycle. At the start of the second cycle alkaline phosphate (enzyme) labeled anti-IgE from the Reagent Wedge was added to the reaction medium followed by a second 30 minute incubation at 37° C. After the second 30-minute incubation, the reaction tube was washed to remove any unbound alkaline phosphatase labeled anti-IgE. Substrate was then added to the washed bead reagent and the light generated was measured by the PMT after a 5-minute incubation at 37° C. in a luminometer. The intensity of the light is proportional to the amount of IgE in the patient sample. The IMMULITE 2000/2500 calibration method employs a stored master curve in conjunction with a two-point adjustment procedure. Units reported are kU/L or mIU/ml.

Results:

Results are calculated using a point-to-point formula method, in which several standards are run. Each standard has a specific concentration and a corresponding signal. A master curve is generated when each standard is connected point-to-point by a straight line. Allergy level is reported in two ways: (a) concentration of IgE kU/L and (b) class (classes are based on concentration); two classifications exist (Standard and Extended). The following is an example of a standard classification: Class 0=<0.35 kU/L, Class 1=0.35-0.7 kU/L, Class 2=0.7-3.5 kU/L, Class 3=3.5-17.5 kU/L, Class 4=17.5-52.5 kU/L, Class 5=52.5-100 kU/L, and Class 6=>100 kU/L. The 3gAllergy assay measures the specific IgE produced by an immune response against that specific allergen. In general, the higher the class is, the higher the concentration of specific IgE in kU/L. This means that a patient is more likely to be allergic to a particular allergen and specific IgE cut off values for allergens vary from allergen to allergen. Results are summarized in Table 1 wherein N=number of samples.

TABLE 1

| | |
|---|---|
| N = 16 | Class 0 |
| N = 4 | Class 1 |
| N = 7 | Class 2 |
| N = 3 | Class 3 |
| N = 1 | Class 4 |
| N = 1 | Class 6 |

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method for determining in a sample the presence and/or amount of an IgE specific for a galactose-α-1,3-galactose epitope, the method comprising:
   (a) providing in combination in a medium:
      (i) the sample,
      (ii) a reagent comprising a conjugate of a macromolecule and a compound selected from the group consisting of linear B2 trisaccharide and derivatives thereof and galactotetraose and derivatives thereof,
   (b) subjecting the combination to conditions for binding of the IgE to the reagent to form a complex, and
   (c) detecting the present and/or amount of the complex, the amount of the complex being related to the presence and/or amount of IgE in the sample.

2. The method according to claim 1 wherein the macromolecule is a protein.

3. The method according to claim 1 wherein the protein is a human protein selected from the group consisting of serum albumins and globulins.

4. The method according to claim 1 wherein the conjugate is bound to a particle.

5. The method according to claim 1 wherein the complex is detected by adding to the medium an antibody for IgE wherein the antibody comprises a label.

6. The method according to claim 5 wherein the label is an enzyme, a fluorescent molecule, a chemiluminescent molecule, a radioisotope or a sensitizer.

7. The method according to claim 1 wherein the compound is selected from the group consisting of linear B2 and derivatives thereof.

8. The method according to claim 1 wherein the compound is selected from the group consisting of galactotetraose and derivatives thereof.

* * * * *